United States Patent
Chen et al.

(10) Patent No.: US 12,311,650 B2
(45) Date of Patent: May 27, 2025

(54) PRESSURE RELIEF CUSHION

(71) Applicant: TRONJEN MEDICAL TECHNOLOGY INC., Taichung (TW)

(72) Inventors: Szu-Hsien Chen, Taichung (TW); Ya-Wen Ku, Taichung (TW); Ren-Shian Wang, Taichung (TW); Chiu-Fang Chen, Taichung (TW)

(73) Assignee: TRONJEN MEDICAL TECHNOLOGY INC., Taichung (TW)

( * ) Notice: Subject to any disclaimer, the term of this patent is extended or adjusted under 35 U.S.C. 154(b) by 1275 days.

(21) Appl. No.: 16/933,815

(22) Filed: Jul. 20, 2020

(65) Prior Publication Data
US 2021/0023814 A1    Jan. 28, 2021

(30) Foreign Application Priority Data

Jul. 22, 2019 (TW) .................. 108125783
Feb. 7, 2020 (TW) .................. 109201392

(51) Int. Cl.
| B32B 5/18 | (2006.01) |
|---|---|
| A61L 15/42 | (2006.01) |
| A61L 15/58 | (2006.01) |
| B29C 44/00 | (2006.01) |
| B32B 7/06 | (2019.01) |
| B32B 7/12 | (2006.01) |
| C08G 18/08 | (2006.01) |
| C08G 18/10 | (2006.01) |
| C08G 18/28 | (2006.01) |
| C08G 18/32 | (2006.01) |

(Continued)

(52) U.S. Cl.
CPC ............. *B32B 5/18* (2013.01); *A61L 15/425* (2013.01); *A61L 15/585* (2013.01); *B29C 44/00* (2013.01); *B32B 7/06* (2013.01); *B32B 7/12* (2013.01); *C08G 18/10* (2013.01); *C08G 18/14* (2013.01); *C08G 18/289* (2013.01); *C08G 18/3206* (2013.01); *C08G 18/61* (2013.01); *C09J 7/21* (2018.01); *C09J 7/243* (2018.01); *C09J 7/25* (2018.01); *B32B 2266/0278* (2013.01); *B32B 2305/022* (2013.01); *B32B 2405/00* (2013.01); *B32B 2556/00* (2013.01); *C08G 2110/0008* (2021.01); *C09J 7/35* (2018.01); *C09J 133/08* (2013.01); *C09J 183/04* (2013.01); *C09J 2423/00* (2013.01); *C09J 2475/00* (2013.01); *C09J 2477/00* (2013.01)

(58) Field of Classification Search
CPC ....................................... C08G 18/10
See application file for complete search history.

(56) References Cited

U.S. PATENT DOCUMENTS

| 2005/0004500 A1* | 1/2005 | Rosser ................. A61B 5/447 602/41 |
|---|---|---|
| 2009/0018480 A1* | 1/2009 | Mager ................. B01J 8/0214 521/159 |

(Continued)

*Primary Examiner* — Ian A Rummel
(74) *Attorney, Agent, or Firm* — HSML P.C.

(57) ABSTRACT

A pressure relief cushion includes an elastic layer which is made from a viscoelastic foam material, an adhesive carrying layer disposed on the elastic layer and including an adhesive portion and a carrier portion for carrying the adhesive portion, a hydrogel layer disposed on the adhesive carrying layer opposite to the elastic layer, and a detachable film disposed on the hydrogel layer opposite to the adhesive carrying layer.

7 Claims, 2 Drawing Sheets

(51) Int. Cl.
    *C08G 18/61*    (2006.01)
    *C09J 7/21*     (2018.01)
    *C09J 7/24*     (2018.01)
    *C09J 7/25*     (2018.01)
    *C09J 7/35*     (2018.01)
    *C09J 133/08*   (2006.01)
    *C09J 183/04*   (2006.01)

(56) References Cited

U.S. PATENT DOCUMENTS

2013/0149502 A1* 6/2013 Dudley ............... B32B 7/12
                                                    428/354
2014/0371692 A1* 12/2014 Cleary ............... A61K 8/042
                                                    424/443

* cited by examiner

PRESSURE RELIEF CUSHION

CROSS-REFERENCE TO RELATED APPLICATION

This application claims priority of Taiwanese Invention Patent Application No. 108125783, filed on Jul. 22, 2019 and Taiwanese Utility Model Patent Application No. 109201392, filed on Feb. 7, 2020.

FIELD

The disclosure relates to a pressure relief cushion, and more particularly to a pressure relief cushion for preventing pressure sores.

BACKGROUND

When patients are hospitalized or bedridden for any significant amount of time, such patients are likely to develop pressure sores or ulcers. Pressure sores are nerve malnutrition and blood circulation disorder caused by long-term pressure or long-term physical and chemical stimuli on local body tissues. Continuous ischemia, anoxia, and malnutrition of the local tissues cause the skin to lose normal functions and lead to festering and necrosis of soft tissues.

Conventional pressure relief cushions or pads generally utilize flexible materials such as foam or springs which allow the cushion or pad to deform and conform to the patient's body. For instance, TW 1586345 B discloses a pressure relief pad for preventing pressure ulcers, which includes a pressure relief layer that includes a foam structure for evenly dissipating forces applied to the skin, a thin film layer that is a hydrophilic thin layer structure for attaching to the skin, and a release paper that has a smooth surface and a rough surface with a pre-determined pattern. The pressure relief pad may reduce the pressure force and the shear force applied to the skin to prevent pressure ulcers from occurring. However, the thin film layer can only reduce the friction caused by the foam structure on the skin or wound, but cannot promote the healing of pressure sores or wounds.

SUMMARY

Therefore, an object of the disclosure is to provide a pressure relief cushion that can alleviate at least one of the drawbacks of the prior art.

The pressure relief cushion includes:
an elastic layer which is made from a viscoelastic foam material;
an adhesive carrying layer disposed on the elastic layer and including an adhesive portion and a carrier portion for carrying the adhesive portion;
a hydrogel layer disposed on the adhesive carrying layer opposite to the elastic layer; and
a detachable film disposed on the hydrogel layer opposite to the adhesive carrying layer.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
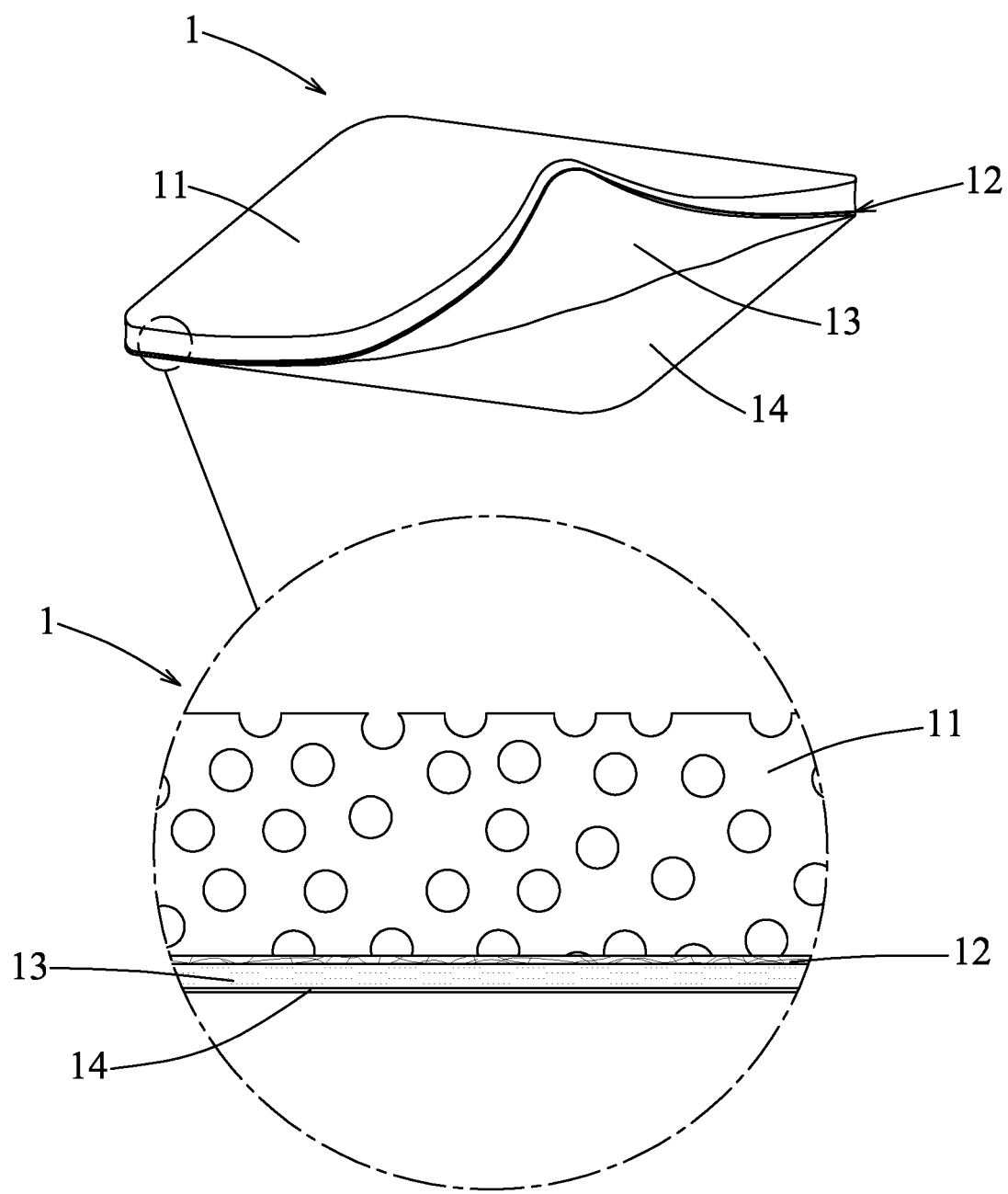
FIG. 1 is a partially exploded view with an enlarged, schematic sectional view to illustrate an example of a pressure relief cushion according to the present disclosure.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a pressure relief cushion, including:
an elastic layer which is made from a viscoelastic foam material;
an adhesive carrying layer disposed on the elastic layer and including an adhesive portion and a carrier portion for carrying the adhesive portion;
a hydrogel layer disposed on the adhesive carrying layer opposite to the elastic layer; and
a detachable film disposed on the hydrogel layer opposite to the adhesive carrying layer.

According to the present disclosure, the elastic layer is made from a flexible cellular polyurethane foam sponge.

According to the present disclosure, the elastic layer is produced by the steps of:
a) reacting a hydrophobic first polyol with a diisocyanate to obtain a diisocyanate-containing prepolymer having a hydrophobic group; and
b) subjecting the diisocyanate-containing prepolymer to a polymerization reaction with a second polyol having a hydrophobic group, a polysiloxane, an aminosilane compound, and a blowing agent, followed by conducting a foaming reaction.

According to the present disclosure, the hydrophobic group of the diisocyanate-containing prepolymer has a weight-average molecular weight ranging from 1,500 g/mol to 6,000 g/mol. In certain embodiments, the hydrophobic group of the diisocyanate-containing prepolymer has a weight-average molecular weight ranging from 2,000 g/mol to 3,000 g/mol.

According to the present disclosure, the hydrophobic groups of the diisocyanate-containing prepolymer and the second polyol are independently selected from the group consisting of polypropylene glycol, polytetrahydrofuran, and a combination thereof.

According to the present disclosure, the hydrophobic group of the second polyol has a weight-average molecular weight ranging from 200 g/mol to 1,000 g/mol.

According to the present disclosure, the polysiloxane has a weight-average molecular weight ranging from 1,000 g/mol to 20,000 g/mol. In certain embodiments of the present disclosure, the polysiloxane is poly(dimethylsiloxane) (PDMS).

According to the present disclosure, the aminosilane compound is selected from the group consisting of (3-aminopropyl)triethoxysilane (APTMS), (3-aminopropyl)

trimethoxysilane (APTMS), 3-aminopropyl(diethoxy)methylsilane (APDEMS), and combinations thereof. In certain embodiments of the present disclosure, the aminosilane compound is APTES.

According to the present disclosure, the elastic layer has a thickness ranging from 1 cm to 10 cm. In certain embodiments, the thickness of the elastic layer ranges from 2.5 cm to 3.0 cm.

In certain embodiments of the present disclosure, the blowing agent is water.

According to the present disclosure, the hydrogel layer is produced by the steps of:
- a1) reacting a polyol having a hydrophobic group with a diisocyanate compound having a hydrophilic group to obtain a first prepolymer;
- b1) partially crosslinking the first prepolymer using a crosslinking agent to obtain a second prepolymer; and
- c1) subjecting the second prepolymer to an end-capping reaction.

According to the present disclosure, the hydrophobic group of the polyol in step (a1) is selected from the group consisting of polypropylene glycol, polytetrahydrofuran, and a combination thereof.

In certain embodiments of the present disclosure, the hydrophilic group of the diisocyanate compound in step (a1) is polyethylene glycol.

In certain embodiments of the present disclosure, the polyol in step (a1) is a hexahydric alcohol.

According to the present disclosure, the hydrogel layer has a thickness ranging from 0.01 cm to 1.00 cm. In certain embodiments, the thickness of the hydrogel layer ranges from 0.20 cm to 0.50 cm.

According to the present disclosure, the carrier portion of the adhesive carrying layer is made from a material selected from the group consisting of polyethylene, polypropylene, polyurethane, polyamide, and combinations thereof.

According to the present disclosure, the adhesive carrying layer is in a form selected from the group consisting of a polymer film and a nonwoven fabric.

According to the present disclosure, the adhesive portion of the adhesive carrying layer is selected from the group consisting of a hot-melt adhesive, an acrylic adhesive, a silicone adhesive, and combinations thereof.

According to the present disclosure, the pressure relief cushion has a resiliency of less than 30% as measured according to ASTM D3574-17 ball rebound test. In certain embodiments, the pressure relief cushion has a resiliency of less than 10% as measured according to ASTM D3574-17 ball rebound test.

According to the present disclosure, the detachable film is not removed until the pressure relief cushion is applied to a human body, so as to prevent the hydrogel layer from being contaminated or reducing adhesion before contacting the skin.

The disclosure will be further described by way of the following examples. However, it should be understood that the following examples are solely intended for the purpose of illustration and should not be construed as limiting the disclosure in practice.

EXAMPLES

Referring to FIG. 1, a pressure relief cushion 1 according to the present disclosure was produced as an example, and included an elastic layer 11 made from a viscoelastic foam material, an adhesive carrying layer 12 disposed on the elastic layer 11 and including an adhesive portion and a carrier portion for carrying the adhesive portion, a hydrogel layer 13 disposed on the adhesive carrying layer 12 opposite to the elastic layer 11, and a detachable film 14 disposed on the hydrogel layer 13 opposite to the adhesive carrying layer 12.

The elastic layer 11 was a cuboid-shaped flexible cellular polyurethane foam sponge having a size of 15 cm (width)× 20 cm (length)×2.5 cm (thickness). The elastic layer 11 was prepared as follows.

In step (a), 2,4-toluene diisocyanate (2,4-TDI) and poly (propylene glycol) diol (PPG 3000 diol) were mixed in a molar ratio of 2:1. The resultant mixture was stirred at 80° C. for 90 minutes under an enclosed nitrogen atmosphere. During the reaction above, analysis was conducted to monitor the presence of the characteristic NCO group (—NCO) peak at 2270 cm$^{-1}$. The characteristic NCO group peak at 2270 cm$^{-1}$ was successfully detected, indicating that a prepolymer containing two isocyanate groups per molecule was obtained.

In step (b), the prepolymer, poly(propylene glycol) triol (PPG 400 triol), water, polydimethylsiloxane (PDMS) (which had a weight-average molecular weight ranging from 1,000 g/mol to 3,000 g/mol), and (3-aminopropyl)triethoxysilane (APTES) were mixed in a molar ratio of 1:1:0.4: 0.3:0.3, and 0.1 wt % of stannous octoate (T9) was then used as a catalyst (based on the total weight of the above-mentioned components). The resultant mixture was stirred at 20° C. for 5 minutes under are enclosed nitrogen atmosphere, followed by standing at 30° C. to 40° C. for 24 hours, so as to obtain the flexible cellular polyurethane foam sponge.

The adhesive carrying layer 12 was in the form of a polyurethane film which was prepared by a blown film process and had a thickness of about 0.7 mm. The carrier portion of the adhesive carrying layer 12 was polyurethane, and the adhesive portion of the adhesive carrying layer 12 was a polyisobutylene rubber hot-melt adhesive.

The hydrogel layer 13 was prepared as follows.

In step (a1), 1,1,1-trimethylolpropane (TMP) and hexamethylene diisocyanate (EDI) were mixed in a molar ratio of 1:3, and 0.05 wt % of triethylenediamine (TEDA) (based on the total weight of TMP and HDI) was then used as a catalyst. The resultant mixture was stirred at 80° C. for 90 minutes under an enclosed nitrogen atmosphere. During the reaction above, FT-IR spectroscopy analysis was conducted to monitor the presence of the characteristic NCO group (—NCO) peak at 2270 cm$^{-1}$. The characteristic NCO group peak at 2270 cm$^{-1}$ was successfully detected, indicating that a triisocyanate intermediate was obtained.

In step (a2), the triisocyanate intermediate and poly (propylene glycol) triol (PPG 4000 triol) were mixed in a molar ratio of 1:3, and 0.05 wt % of TEDA (based on the total weight of the triisocyanate intermediate and PPG 4000 triol) was then used as a catalyst. The resultant mixture was stirred at 80° C. for 90 minutes under an enclosed nitrogen atmosphere. During the reaction above, FT-IR spectroscopy analysis was performed as described in step (a1). The characteristic NCO group peak at 2270 cm$^{-1}$ was not detected, indicating that a hydrophobic hexahydric alcohol which contained polypropylene glycol was obtained.

In step (b), poly(ethylene glycol) diol (PEG 1000 diol) and HDI were mixed in a molar ratio of 1:2, and 0.05 wt % of TEDA (based on the total weight of PEG 1000 diol and HDI) was then used as a catalyst. The resultant mixture was stirred at 80° C. for 90 minutes under an enclosed nitrogen atmosphere. During the reaction above, FT-IR spectroscopy analysis was performed as described in step (a1). The characteristic NCO group peak at 2270 cm$^{-1}$ was successfully detected, indicating that a hydrophilic diisocyanate compound which contained polyethylene glycol was obtained.

In step (c), the hydrophobic hexahydric alcohol and the hydrophilic diisocyanate compound were mixed in a molar ratio of 1:6, followed by stirring at 80° C. for 90 minutes under an enclosed nitrogen atmosphere. During the reaction above, FT-IR spectroscopy analysis was performed as described in step (a1). The characteristic NCO group peak at 2270 cm$^{-1}$ was successfully detected, indicating that a first prepolymer which included 6 isocyanate groups was obtained. The first prepolymer had a hydrophobic interior and a hydrophilic exterior.

In step (d), the first prepolymer and poly(ethylene glycol) diamine (PEG diamine 5000, acting as a crosslinking agent) were mixed in a molar ratio of 2:0.2, followed by stirring at 80° C. for 90 minutes under an enclosed nitrogen atmosphere. During the cross-linking reaction above, FT-IR spectroscopy analysis was performed as described in step (a1). The characteristic NCO group peak at 2270 cm$^{-1}$ was successfully detected, indicating that a second prepolymer which included 3 to 6 isocyanate groups was obtained. The second prepolymer had a weight average molecular weight of 52,000 g/mol.

In step (e), the second prepolymer and (3-aminopropyl)triethoxysilane (APTES) were mixed in a molar ratio of 1:0.8, followed by stirring at 80° C. for 90 minutes under an enclosed nitrogen atmosphere. During the end-capping reaction above, FT-IR spectroscopy analysis was performed as described in step (a1). The characteristic NCO group peak at 2270 cm$^{-1}$ was not detected, indicating that the hydrogel layer 13 was obtained. The hydrogel layer 13 had a thickness of about 0.25 mm.

The pressure relief cushion 1 was produced by the steps of: adhering the adhesive carrying layer 12 to the elastic layer 11, coating the hydrogel layer 13 on the adhesive carrying layer 12 opposite to the elastic layer 11, and bringing the detachable film 14 to cover the hydrogel layer 13 opposite to the adhesive carrying layer 12.

The resiliency of the pressure relief cushion 1 thus prepared was measured according to ASTM D3574-17 ball rebound test. The experimental result showed that the pressure relief cushion 1 had a resiliency of about 3%.

Figure 2:
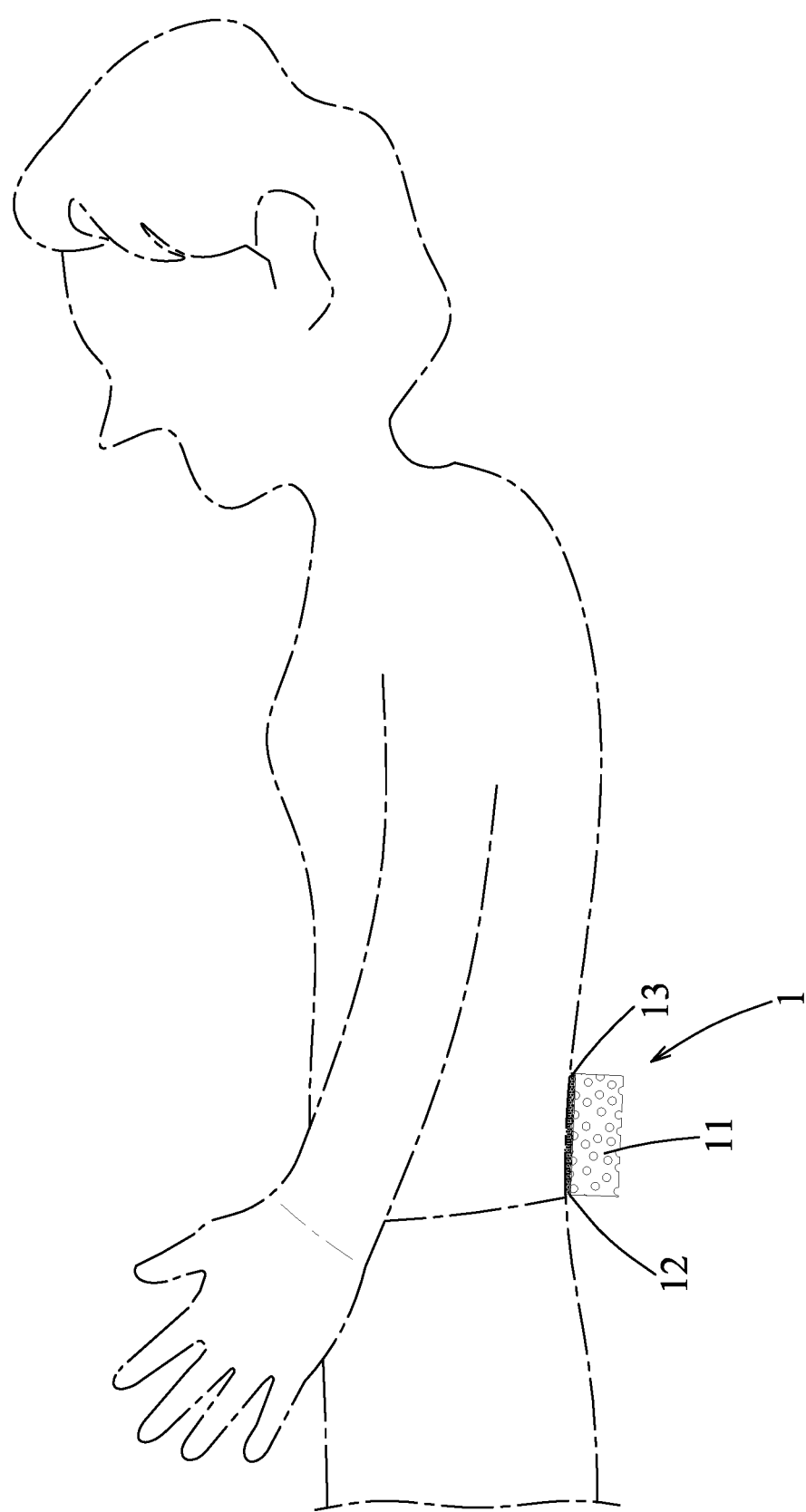
FIG. 2 is a schematic view illustrating that the example is applied to a human body.

Referring to FIG. 2, when the pressure relief cushion 1 of this example is to be applied to a human body of a user, the detachable film 14 is torn off from the hydrogel layer 13, and the elastic layer 11, the adhesive carrying layer 12, and the hydrogel layer 13 are attached to the human body in an integrated manner by adhering the hydrogel layer 13 to the skin of the sacrum. Therefore, when the user sits or lies down, the pressure relief cushion 1 can prevent undesired continuous exertion of pressure on some part of the human body, thereby reducing the occurrence probability of pressure ulcers and promoting the healing of pressure sores or wounds.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A pressure relief cushion, comprising:
    an elastic layer made from a viscoelastic foam material;
    an adhesive carrying layer disposed on said elastic layer and comprising an adhesive portion and a carrier portion for carrying said adhesive portion;
    a hydrogel layer disposed on said adhesive carrying layer opposite to said elastic layer; and
    a detachable film disposed on said hydrogel layer opposite to said adhesive carrying layer,
    wherein the pressure relief cushion has a resiliency of less than 10% as measured according to ASTM D3574-17 ball rebound test, said adhesive portion of said adhesive carrying layer being a polyisobutylene rubber hot-melt adhesive.

2. The pressure relief cushion according to claim 1, wherein said elastic layer is made from a flexible cellular polyurethane foam sponge.

3. The pressure relief cushion according to claim 1, wherein said elastic layer has a thickness ranging from 1 cm to 10 cm.

4. The pressure relief cushion according to claim 1, wherein said hydrogel layer has a thickness ranging from 0.01 cm to 1.00 cm.

5. The pressure relief cushion according to claim 1, wherein said carrier portion of said adhesive carrying layer is made from a material selected from the group consisting of polyethylene, polypropylene, polyurethane, polyamide, and combinations thereof.

6. The pressure relief cushion according to claim 1, wherein said adhesive carrying layer is in a form selected from the group consisting of a polymer film and a nonwoven fabric.

7. The pressure relief cushion according to claim 1, which has a resiliency of about 3% as measured according to ASTM D3574-17 ball rebound test.

* * * * *